US005731194A

United States Patent [19]

Kalman et al.

[11] Patent Number: 5,731,194
[45] Date of Patent: Mar. 24, 1998

[54] INSECTICIDE PROTEIN AND GENE

[75] Inventors: Sue S. Kalman, Saratoga; Kristine L. Kiehne, San Jose, both of Calif.

[73] Assignee: Sandoz Ltd., Basel, Switzerland

[21] Appl. No.: 457,366

[22] Filed: Jun. 1, 1995

Related U.S. Application Data

[63] Continuation of Ser. No. 197,998, Feb. 16, 1994, abandoned, which is a continuation of Ser. No. 102,316, Aug. 5, 1993, abandoned, which is a continuation of Ser. No. 4,474, Jan. 14, 1993, abandoned, which is a continuation of Ser. No. 844,302, Feb. 27, 1992, abandoned.

[51] Int. Cl.[6] .................... C12N 1/20; C12N 5/14; C12N 15/32; C12N 15/63; C07K 14/325

[52] U.S. Cl. .................... 435/240.4; 435/240.1; 435/252.3; 435/254.11; 435/320.1; 536/23.71; 530/350

[58] Field of Search .................... 530/350; 536/23.71; 435/320.1, 240.1, 252.3, 240.4, 252.33, 254.11

[56] References Cited

PUBLICATIONS

Schnepf, H. et al., 1985 "Amino Acid Sequence of a Crystal Protein from *Bacillus thuringiensis* Deduced . . . " J. Biol. Chem. 260:6264–6272.

Honee, G. et al. 1985 "Nucleotide Sequence of Crystal Protein Gene isolated from *B. thuringiensis* subspecies . . . " Nucl. Acids Res. 16(13):6240.

Hofte, H. et al. 1990 "Nucleotide Sequence and Deduced Amino Acid Sequence of a New Lepidoptera–Specific . . . " Nucl. Acids Res. 18(18):5545.

Hofte, H. et al. 1986 "Structure and Functional Analysis of a Cloned Delta Endotoxin of *B. thuringiensis* berliner" Eur. J. Biochem. 161:273–280.

Visser, B. et al. 1990 "A Novel *Bacillus thuringiensis* Gene Encoding a *Spodoptera exigua*–Specific Crystal Protein" J. Bact. 172(12):6783–6788.

Bossse et al. 1990 "Nucleotide Sequence of a Novel Crystal Protein Gene Isolated from *B. thuringiensis* subspecies *kenyae*" Nucl. Acids Res. 18(24):2243.

Adang M. et al. 1985 "Characterized Full–Length and Truncated Plasmid Clones of the Crystal Protein . . . "0 Gene 36:289–300.

Brizzard, B. et al. 1988 "Nucleotide Sequence of an Additional Crystal Protein Gene Cloned . . . " Nucl. Acids Res. 16(6):2723.

Kalman et al. App Envir. Micb. 59(4) 1131–1137 1993.

Prefontaine App Envir Micb. 53 2808–14 (1987).

Haider et al Gene S2 285–298 (1987).

*Primary Examiner*—Dian C. Jacobson
*Assistant Examiner*—Gabriele E. Bugaisky
*Attorney, Agent, or Firm*—Lynn Marcus-Wyner

[57] ABSTRACT

A novel insecticidal protein isolated from *Bacillus thuringiensis* var. galleria is described and its DNA sequence is given. This protein, called CryIC(b), is toxic to Lepidoptera, including Spodoptera.

18 Claims, 3 Drawing Sheets

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 4106 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 296..3826
        ( D ) OTHER INFORMATION: /codon_start= 296

( x i ) SEQUENCE DESCRIPTION: SEQ ID NO:1:

```
TAGATTTTAT ATAAGTATAA AAAATAATAA GACTTTAATA TAAGTTAAGG GAATACAAAT        60

CCTTAATGCA TTGGTTAAAT ATTATAAACT CTAAAGCATG GATGATGGTT GAGAAGTAAG       120

TAGATTATTA ACACCCTGGG TCTATTTTAG CCCCAGGGTA TAAATTGATA TTTAATAAAA       180

TCGGTTGCAC TTTGAGTATT TTTTCATAGA ATGACTCATA TGATTAACAT TGCAATACAG       240

TAAAAGATCT TTAGTTATAA AGAAAAACTA TTACGCTAAA AAGTGGAGGG AACAT ATG        298
                                                               Met
                                                                1

GAG AAT AAT ATT CAA AAT CAA TGC GTA CCT TAC AAT TGT TTA AGT AAT        346
Glu Asn Asn Ile Gln Asn Gln Cys Val Pro Tyr Asn Cys Leu Ser Asn
          5               10                  15

CCT GAG GAG ATA CTT TTA GAT GGA GAA AGA ATA TCA ACT GGT AAT TCA        394
Pro Glu Glu Ile Leu Leu Asp Gly Glu Arg Ile Ser Thr Gly Asn Ser
    20                  25                  30

TCA ATT GAT ATC TCT CTG TCA CTT GTC CAG CTT CTG GTA TCT AAC TTT        442
Ser Ile Asp Ile Ser Leu Ser Leu Val Gln Leu Leu Val Ser Asn Phe
35                  40                  45

GTA CCA GGG GGA GGA TTT TTA GTT GGA TTA TTA GAT TTT GTA TGG GGA        490
Val Pro Gly Gly Gly Phe Leu Val Gly Leu Leu Asp Phe Val Trp Gly
50                  55                  60                  65

ATA GTA GGC CCT TCT CCA TGG GAT GCA TTT CTA GTG CAA ATT GAA CAA        538
Ile Val Gly Pro Ser Pro Trp Asp Ala Phe Leu Val Gln Ile Glu Gln
                70                  75                  80

TTA ATT AAT GAA AGA ATA GCT GCA TAT GCT AGG TCT GCA GCA ATT TCT        586
Leu Ile Asn Glu Arg Ile Ala Ala Tyr Ala Arg Ser Ala Ala Ile Ser
            85                  90                  95

AAT TTA GAA GGA TTA GGA AAC AAT TTC AAT ATA TAT GTG GAA GCA TTT        634
Asn Leu Glu Gly Leu Gly Asn Asn Phe Asn Ile Tyr Val Glu Ala Phe
        100                 105                 110
```

| | | | | | | | | | | | | | | | | |
|---|---|---|---|---|---|---|---|---|---|---|---|---|---|---|---|---|
| AAA | GAA | TGG | GAA | GCA | GAT | CCT | GAT | AAT | CCA | GTA | ACC | AGG | ACT | AGA | GTA | 682 |
| Lys | Glu | Trp | Glu | Ala | Asp | Pro | Asp | Asn | Pro | Val | Thr | Arg | Thr | Arg | Val | |
| 115 | | | | | 120 | | | | | 125 | | | | | | |
| GTT | GAT | CGC | TTT | CGT | ATA | CTT | GAT | GGG | CTA | CTT | GAA | AGG | GAC | ATC | CCT | 730 |
| Val | Asp | Arg | Phe | Arg | Ile | Leu | Asp | Gly | Leu | Leu | Glu | Arg | Asp | Ile | Pro | |
| 130 | | | | | 135 | | | | | 140 | | | | | 145 | |
| TCA | TTT | CGA | ATT | GCT | GGA | TTT | GAA | GTA | CCC | CTT | TTA | TCC | GTT | TAT | GCT | 778 |
| Ser | Phe | Arg | Ile | Ala | Gly | Phe | Glu | Val | Pro | Leu | Leu | Ser | Val | Tyr | Ala | |
| | | | | 150 | | | | | 155 | | | | | 160 | | |
| CAA | GCG | GCC | AAT | TTG | CAT | CTA | GCT | ATA | TTA | AGA | GAT | TCT | TCA | ATT | TTT | 826 |
| Gln | Ala | Ala | Asn | Leu | His | Leu | Ala | Ile | Leu | Arg | Asp | Ser | Ser | Ile | Phe | |
| | | | 165 | | | | 170 | | | | | 175 | | | | |
| GGA | GCA | AGA | TGG | GGA | TTG | ACA | ACA | ATA | AAT | GTC | AAT | GAA | AAC | TAT | AAT | 874 |
| Gly | Ala | Arg | Trp | Gly | Leu | Thr | Thr | Ile | Asn | Val | Asn | Glu | Asn | Tyr | Asn | |
| | | 180 | | | | | 185 | | | | | 190 | | | | |
| AGG | CTA | ATT | AGG | CAT | ATT | GAT | GAA | TAT | GCT | AAT | CAC | TGT | GCA | GAT | ACG | 922 |
| Arg | Leu | Ile | Arg | His | Ile | Asp | Glu | Tyr | Ala | Asn | His | Cys | Ala | Asp | Thr | |
| | 195 | | | | | 200 | | | | | 205 | | | | | |
| TAT | AAT | CGG | GGA | TTA | AAT | AAT | TTA | CCA | AAA | TCT | ACG | TAT | CAA | GAT | TGG | 970 |
| Tyr | Asn | Arg | Gly | Leu | Asn | Asn | Leu | Pro | Lys | Ser | Thr | Tyr | Gln | Asp | Trp | |
| 210 | | | | | 215 | | | | | 220 | | | | | 225 | |
| ATA | ACA | TAT | AAT | CGA | TTA | CGG | AGA | GAC | TTA | ACA | TTA | ACT | GTA | TTA | GAT | 1018 |
| Ile | Thr | Tyr | Asn | Arg | Leu | Arg | Arg | Asp | Leu | Thr | Leu | Thr | Val | Leu | Asp | |
| | | | | 230 | | | | | 235 | | | | | 240 | | |
| ATC | GCT | GCT | TTC | TTT | CCA | AGC | TAT | GAC | AAT | AGG | AGA | TAT | CCA | ATT | CAG | 1066 |
| Ile | Ala | Ala | Phe | Phe | Pro | Ser | Tyr | Asp | Asn | Arg | Arg | Tyr | Pro | Ile | Gln | |
| | | | 245 | | | | | 250 | | | | | 255 | | | |
| TCA | GTT | GGT | CAA | CTA | ACA | AGG | GAA | ATT | TAT | ACG | GAC | CCA | TTA | ATT | ACT | 1114 |
| Ser | Val | Gly | Gln | Leu | Thr | Arg | Glu | Ile | Tyr | Thr | Asp | Pro | Leu | Ile | Thr | |
| | | 260 | | | | | 265 | | | | | 270 | | | | |
| TTT | AAT | CCA | CAG | TTA | CAG | TCT | GTA | GCT | CAA | TTA | CCT | ACT | TTT | AAC | GTT | 1162 |
| Phe | Asn | Pro | Gln | Leu | Gln | Ser | Val | Ala | Gln | Leu | Pro | Thr | Phe | Asn | Val | |
| | 275 | | | | | 280 | | | | | 285 | | | | | |
| ATG | GAA | AGC | AAC | GCA | ATT | AGA | ACT | CCT | CAT | TTA | TTT | GAT | GTA | TTG | AAT | 1210 |
| Met | Glu | Ser | Asn | Ala | Ile | Arg | Thr | Pro | His | Leu | Phe | Asp | Val | Leu | Asn | |
| 290 | | | | | 295 | | | | | 300 | | | | | 305 | |
| AAT | CTT | ACA | ATT | TTT | ACA | GAT | TGG | TTT | AGT | GTT | GGA | CGC | AAC | TTT | TAT | 1258 |
| Asn | Leu | Thr | Ile | Phe | Thr | Asp | Trp | Phe | Ser | Val | Gly | Arg | Asn | Phe | Tyr | |
| | | | | 310 | | | | | 315 | | | | | 320 | | |
| TGG | GGA | GGA | CAT | CGA | GTA | ATA | TCT | AAC | CGT | ATA | GGA | GGA | GGT | AAC | ATA | 1306 |
| Trp | Gly | Gly | His | Arg | Val | Ile | Ser | Asn | Arg | Ile | Gly | Gly | Gly | Asn | Ile | |
| | | | 325 | | | | | 330 | | | | | 335 | | | |
| ACA | TCT | CCT | ATA | TAT | GGA | AGA | GAG | GCG | AAT | CAG | GAG | CCT | CCA | AGA | TCT | 1354 |
| Thr | Ser | Pro | Ile | Tyr | Gly | Arg | Glu | Ala | Asn | Gln | Glu | Pro | Pro | Arg | Ser | |
| | | 340 | | | | | 345 | | | | | 350 | | | | |
| TTT | ACT | TTT | AAT | GGG | CCT | GTT | TTT | AGG | ACT | TTA | TCA | AAT | CCT | ACT | TTT | 1402 |
| Phe | Thr | Phe | Asn | Gly | Pro | Val | Phe | Arg | Thr | Leu | Ser | Asn | Pro | Thr | Phe | |
| | | 355 | | | | | 360 | | | | | 365 | | | | |
| AGA | CCT | TTA | CAG | CAA | CCT | TGG | CCA | GCG | CCA | CCA | TTT | AAT | TTA | CGT | GGT | 1450 |
| Arg | Pro | Leu | Gln | Gln | Pro | Trp | Pro | Ala | Pro | Pro | Phe | Asn | Leu | Arg | Gly | |
| 370 | | | | | 375 | | | | | 380 | | | | | 385 | |
| GTT | GAA | GGA | GTA | GAA | TTT | TCT | ACA | CCT | TTA | AAT | AGC | TTT | ACG | TAT | CGA | 1498 |
| Val | Glu | Gly | Val | Glu | Phe | Ser | Thr | Pro | Leu | Asn | Ser | Phe | Thr | Tyr | Arg | |
| | | | | 390 | | | | | 395 | | | | | 400 | | |
| GGA | AGA | GGT | ACG | GTT | GAT | TCT | TTA | ACT | GAG | TTA | CCG | CCT | GAG | GAT | AAT | 1546 |
| Gly | Arg | Gly | Thr | Val | Asp | Ser | Leu | Thr | Glu | Leu | Pro | Pro | Glu | Asp | Asn | |
| | | | 405 | | | | | 410 | | | | | 415 | | | |
| AGT | GTG | CCT | CCT | CGC | GAA | GGA | TAT | AGT | CAT | CGT | TTA | TGT | CAT | GCA | ACT | 1594 |
| Ser | Val | Pro | Pro | Arg | Glu | Gly | Tyr | Ser | His | Arg | Leu | Cys | His | Ala | Thr | |
| | | 420 | | | | | 425 | | | | | 430 | | | | |

| | | | | | | | | | | | | | | | | |
|---|---|---|---|---|---|---|---|---|---|---|---|---|---|---|---|---|
| TTT | GTT | CAA | AGA | TCT | GGA | ACC | CCA | TTT | TTA | ACA | ACT | GGT | CCA | GTA | TTT | 1642 |
| Phe | Val | Gln | Arg | Ser | Gly | Thr | Pro | Phe | Leu | Thr | Thr | Gly | Pro | Val | Phe | |
| | 435 | | | | 440 | | | | | | 445 | | | | | |
| TCT | TGG | ACG | CAT | CGT | AGT | GCT | ACT | GAT | CGA | AAT | ATA | ATC | TAC | CCG | GAT | 1690 |
| Ser | Trp | Thr | His | Arg | Ser | Ala | Thr | Asp | Arg | Asn | Ile | Ile | Tyr | Pro | Asp | |
| 450 | | | | | 455 | | | | | 460 | | | | | 465 | |
| GTA | ATT | AAC | CAA | ATA | CCG | TTA | GTA | AAA | GCA | TTC | AAC | CTT | ACT | TCA | GGT | 1738 |
| Val | Ile | Asn | Gln | Ile | Pro | Leu | Val | Lys | Ala | Phe | Asn | Leu | Thr | Ser | Gly | |
| | | | | 470 | | | | | 475 | | | | | 480 | | |
| ACC | TCT | GTA | GTC | AGA | GGT | CCA | GGA | TTT | ACA | GGA | GGG | GAT | ATC | ATC | CGA | 1786 |
| Thr | Ser | Val | Val | Arg | Gly | Pro | Gly | Phe | Thr | Gly | Gly | Asp | Ile | Ile | Arg | |
| | | | 485 | | | | | 490 | | | | | 495 | | | |
| ACT | AAC | GTT | AAT | GGT | AGT | GTA | CTA | AGT | ATG | AGT | CTT | AAT | TTT | AGT | AAC | 1834 |
| Thr | Asn | Val | Asn | Gly | Ser | Val | Leu | Ser | Met | Ser | Leu | Asn | Phe | Ser | Asn | |
| | | 500 | | | | | 505 | | | | | 510 | | | | |
| ACA | ACA | TTA | CAG | CGG | TAT | CGT | GTG | AGA | GTT | CGT | TAT | GCT | GCT | TCT | CAA | 1882 |
| Thr | Thr | Leu | Gln | Arg | Tyr | Arg | Val | Arg | Val | Arg | Tyr | Ala | Ala | Ser | Gln | |
| | 515 | | | | | 520 | | | | | 525 | | | | | |
| ACA | ATG | GTC | ATG | AGC | GTA | ACT | GTT | GGA | GGG | AGT | ACT | ACT | GGT | AAT | CAA | 1930 |
| Thr | Met | Val | Met | Ser | Val | Thr | Val | Gly | Gly | Ser | Thr | Thr | Gly | Asn | Gln | |
| 530 | | | | | 535 | | | | | 540 | | | | | 545 | |
| GGA | TTC | CCT | AGT | ACT | ATG | AGT | GCA | AAT | GGG | GCT | TTG | ACA | TCT | CAA | TCA | 1978 |
| Gly | Phe | Pro | Ser | Thr | Met | Ser | Ala | Asn | Gly | Ala | Leu | Thr | Ser | Gln | Ser | |
| | | | | 550 | | | | | 555 | | | | | 560 | | |
| TTT | AGA | TTC | GCA | GAA | TTT | CCT | GTA | GGT | ATT | AGT | GCA | TCT | GGC | AGT | CAA | 2026 |
| Phe | Arg | Phe | Ala | Glu | Phe | Pro | Val | Gly | Ile | Ser | Ala | Ser | Gly | Ser | Gln | |
| | | 565 | | | | | 570 | | | | | 575 | | | | |
| GGT | GCA | TCA | ATA | AGT | ATT | AGT | AAT | AAT | GTA | GGT | AGA | CAA | ATG | TTT | CAC | 2074 |
| Gly | Ala | Ser | Ile | Ser | Ile | Ser | Asn | Asn | Val | Gly | Arg | Gln | Met | Phe | His | |
| | | 580 | | | | | 585 | | | | | 590 | | | | |
| TTA | GAT | AGA | ATT | GAA | TTT | CTC | CCA | GTT | ACT | TCT | ACA | TTT | GAG | GAG | GAA | 2122 |
| Leu | Asp | Arg | Ile | Glu | Phe | Leu | Pro | Val | Thr | Ser | Thr | Phe | Glu | Glu | Glu | |
| | 595 | | | | | 600 | | | | | 605 | | | | | |
| TAT | GAT | TTA | GAA | AGA | GCG | CAA | GAG | GCG | GTG | AAT | GCC | CTG | TTT | ACT | TCT | 2170 |
| Tyr | Asp | Leu | Glu | Arg | Ala | Gln | Glu | Ala | Val | Asn | Ala | Leu | Phe | Thr | Ser | |
| 610 | | | | | 615 | | | | | 620 | | | | | 625 | |
| ACG | AAC | CAA | CTA | GGG | CTA | AAA | ACA | GAT | GTA | ACG | GAT | TAT | CAT | ATT | GAT | 2218 |
| Thr | Asn | Gln | Leu | Gly | Leu | Lys | Thr | Asp | Val | Thr | Asp | Tyr | His | Ile | Asp | |
| | | | | 630 | | | | | 635 | | | | | 640 | | |
| CAA | GTA | TCA | AAT | CTA | GTT | GAA | TGC | TTA | TCG | GAT | GAA | TTT | TGT | CTG | GAT | 2266 |
| Gln | Val | Ser | Asn | Leu | Val | Glu | Cys | Leu | Ser | Asp | Glu | Phe | Cys | Leu | Asp | |
| | | | 645 | | | | | 650 | | | | | 655 | | | |
| GAA | AAG | CGA | GAA | TTG | TCT | GAG | AAA | GTC | AAA | CAT | GCG | AAG | CGA | CTC | AGC | 2314 |
| Glu | Lys | Arg | Glu | Leu | Ser | Glu | Lys | Val | Lys | His | Ala | Lys | Arg | Leu | Ser | |
| | | 660 | | | | | 665 | | | | | 670 | | | | |
| GAT | GAG | CGC | AAT | TTA | CTC | CAG | GAT | CGA | AAT | TTC | AGA | TCC | ATT | AAT | GGG | 2362 |
| Asp | Glu | Arg | Asn | Leu | Leu | Gln | Asp | Arg | Asn | Phe | Arg | Ser | Ile | Asn | Gly | |
| | 675 | | | | | 680 | | | | | 685 | | | | | |
| CAA | CTA | GAC | CGT | GGC | TGG | AGA | GGA | AGT | ACG | GAT | ATT | ACC | ATC | CAA | GGT | 2410 |
| Gln | Leu | Asp | Arg | Gly | Trp | Arg | Gly | Ser | Thr | Asp | Ile | Thr | Ile | Gln | Gly | |
| 690 | | | | | 695 | | | | | 700 | | | | | 705 | |
| GGA | GAT | GAC | GTA | TTC | AAA | GAG | AAT | TAC | GTC | ACA | CTG | CCG | GGT | ACC | TTT | 2458 |
| Gly | Asp | Asp | Val | Phe | Lys | Glu | Asn | Tyr | Val | Thr | Leu | Pro | Gly | Thr | Phe | |
| | | | | 710 | | | | | 715 | | | | | 720 | | |
| GAT | GAG | TGC | TAT | CCA | ACG | TAT | CTA | TAT | CAA | AAA | ATA | GAT | GAA | TCG | AAA | 2506 |
| Asp | Glu | Cys | Tyr | Pro | Thr | Tyr | Leu | Tyr | Gln | Lys | Ile | Asp | Glu | Ser | Lys | |
| | | | 725 | | | | | 730 | | | | | 735 | | | |
| TTA | AAA | TCC | TAT | ACA | CGT | TAC | GAG | TTA | AGA | GGG | TAT | ATC | GAG | GAT | AGT | 2554 |
| Leu | Lys | Ser | Tyr | Thr | Arg | Tyr | Glu | Leu | Arg | Gly | Tyr | Ile | Glu | Asp | Ser | |
| | | 740 | | | | | 745 | | | | | 750 | | | | |

| | | | | | | | | | | | | | | | | |
|---|---|---|---|---|---|---|---|---|---|---|---|---|---|---|---|---|
| CAA | GAT | TTA | GAA | ATC | TAT | TTG | ATT | CGC | TAC | AAT | GCA | AAA | CAC | GAA | ATA | 2602 |
| Gln | Asp | Leu | Glu | Ile | Tyr | Leu | Ile | Arg | Tyr | Asn | Ala | Lys | His | Glu | Ile | |
| | 755 | | | | 760 | | | | | 765 | | | | | | |
| GTA | AAT | GTA | CCA | GGT | ACA | GGG | AGT | TTA | TGG | CCT | CTT | TCT | ATA | GAA | AAT | 2650 |
| Val | Asn | Val | Pro | Gly | Thr | Gly | Ser | Leu | Trp | Pro | Leu | Ser | Ile | Glu | Asn | |
| 770 | | | | | 775 | | | | | 780 | | | | | 785 | |
| TCA | ATT | GGG | CCT | TGT | GGA | GAA | CCG | AAT | CGC | TGC | GCG | CCA | CAC | CTT | GAA | 2698 |
| Ser | Ile | Gly | Pro | Cys | Gly | Glu | Pro | Asn | Arg | Cys | Ala | Pro | His | Leu | Glu | |
| | | | | 790 | | | | | 795 | | | | | 800 | | |
| TGG | AAT | CCT | AAT | CTA | GAT | TGT | TCC | TGC | AGG | GAC | GGG | GAA | AAA | TGT | GCC | 2746 |
| Trp | Asn | Pro | Asn | Leu | Asp | Cys | Ser | Cys | Arg | Asp | Gly | Glu | Lys | Cys | Ala | |
| | | | 805 | | | | 810 | | | | | 815 | | | | |
| CAT | CAT | TCC | CAT | CAT | TTC | TCC | TTG | GAC | ATT | GAT | GTT | GGA | TGT | ACA | GAC | 2794 |
| His | His | Ser | His | His | Phe | Ser | Leu | Asp | Ile | Asp | Val | Gly | Cys | Thr | Asp | |
| | | 820 | | | | 825 | | | | | 830 | | | | | |
| TTA | AAT | GAG | GAC | TTA | GGT | GTA | TGG | GTG | ATC | TTC | AAG | ATT | AAG | ACG | CAA | 2842 |
| Leu | Asn | Glu | Asp | Leu | Gly | Val | Trp | Val | Ile | Phe | Lys | Ile | Lys | Thr | Gln | |
| | 835 | | | | 840 | | | | | 845 | | | | | | |
| GAT | GGC | CAT | GCA | AGA | CTA | GGA | AAT | CTA | GAG | TTT | CTC | GAA | GAG | AAA | CCA | 2890 |
| Asp | Gly | His | Ala | Arg | Leu | Gly | Asn | Leu | Glu | Phe | Leu | Glu | Glu | Lys | Pro | |
| 850 | | | | | 855 | | | | | 860 | | | | | 865 | |
| CTA | TTA | GGG | GAA | GCA | CTA | GCT | CGT | GTG | AAA | AGA | GCG | GAG | AAG | AAA | TGG | 2938 |
| Leu | Leu | Gly | Glu | Ala | Leu | Ala | Arg | Val | Lys | Arg | Ala | Glu | Lys | Lys | Trp | |
| | | | | 870 | | | | | 875 | | | | | 880 | | |
| AGA | GAC | AAA | CGT | GAA | AAA | TTG | GAA | TGG | GAA | ACA | AAT | ATT | GTT | TAT | AAA | 2986 |
| Arg | Asp | Lys | Arg | Glu | Lys | Leu | Glu | Trp | Glu | Thr | Asn | Ile | Val | Tyr | Lys | |
| | | | 885 | | | | 890 | | | | | 895 | | | | |
| GAG | GCA | AAA | GAA | TCT | GTA | GAT | GCT | TTA | TTT | GTG | AAC | TCT | CAA | TAT | GAT | 3034 |
| Glu | Ala | Lys | Glu | Ser | Val | Asp | Ala | Leu | Phe | Val | Asn | Ser | Gln | Tyr | Asp | |
| | | 900 | | | | 905 | | | | | 910 | | | | | |
| AGA | TTA | CAA | GCG | GAT | ACG | AAT | ATC | GCG | ATG | ATT | CAT | GCG | GCA | GAT | AAA | 3082 |
| Arg | Leu | Gln | Ala | Asp | Thr | Asn | Ile | Ala | Met | Ile | His | Ala | Ala | Asp | Lys | |
| | 915 | | | | 920 | | | | | 925 | | | | | | |
| CGC | GTT | CAT | AGA | ATT | AGA | GAA | GCA | TAC | CTT | CCA | GAA | TTA | TCT | GTA | ATT | 3130 |
| Arg | Val | His | Arg | Ile | Arg | Glu | Ala | Tyr | Leu | Pro | Glu | Leu | Ser | Val | Ile | |
| 930 | | | | | 935 | | | | | 940 | | | | | 945 | |
| CCG | GGT | GTA | AAT | GCG | GGC | ATT | TTC | GAA | GAA | TTA | GAG | GGA | CGC | ATT | TTC | 3178 |
| Pro | Gly | Val | Asn | Ala | Gly | Ile | Phe | Glu | Glu | Leu | Glu | Gly | Arg | Ile | Phe | |
| | | | | 950 | | | | | 955 | | | | | 960 | | |
| ACA | GCC | TAC | TCT | CTA | TAT | GAT | GCG | AGA | AAT | GTC | ATT | AAA | AAT | GGC | GAT | 3226 |
| Thr | Ala | Tyr | Ser | Leu | Tyr | Asp | Ala | Arg | Asn | Val | Ile | Lys | Asn | Gly | Asp | |
| | | | 965 | | | | 970 | | | | | 975 | | | | |
| TTC | AAT | AAT | GGT | TTA | TTA | TGC | TGG | AAC | TTG | AAA | GGG | CAT | GTA | GAT | GTA | 3274 |
| Phe | Asn | Asn | Gly | Leu | Leu | Cys | Trp | Asn | Leu | Lys | Gly | His | Val | Asp | Val | |
| | | 980 | | | | 985 | | | | | 990 | | | | | |
| GAA | GAA | CAA | AAC | AAC | CAT | CGT | TCA | GTC | CTT | GTT | GTC | CCG | GAA | TGG | GAA | 3322 |
| Glu | Glu | Gln | Asn | Asn | His | Arg | Ser | Val | Leu | Val | Val | Pro | Glu | Trp | Glu | |
| | 995 | | | | 1000 | | | | | 1005 | | | | | | |
| GCA | GAG | GTG | TCC | CAA | GAA | GTT | CGT | GTC | TGT | CCA | GGT | CGT | GGC | TAT | ATC | 3370 |
| Ala | Glu | Val | Ser | Gln | Glu | Val | Arg | Val | Cys | Pro | Gly | Arg | Gly | Tyr | Ile | |
| 1010 | | | | | 1015 | | | | | 1020 | | | | | 1025 | |
| CTT | CGT | GTT | ACA | GCG | TAC | AAA | GAG | GGA | TAT | GGA | GAG | GGC | TGC | GTA | ACC | 3418 |
| Leu | Arg | Val | Thr | Ala | Tyr | Lys | Glu | Gly | Tyr | Gly | Glu | Gly | Cys | Val | Thr | |
| | | | | 1030 | | | | | 1035 | | | | | 1040 | | |
| ATT | CAT | GAG | ATC | GAA | GAC | AAT | ACA | GAC | GAA | CTG | AAA | TTT | AGC | AAC | TGT | 3466 |
| Ile | His | Glu | Ile | Glu | Asp | Asn | Thr | Asp | Glu | Leu | Lys | Phe | Ser | Asn | Cys | |
| | | | 1045 | | | | 1050 | | | | | 1055 | | | | |
| GTT | GAA | GAG | GAA | GTA | TAT | CCA | AAC | AAC | ACG | GTA | ACG | TGT | AAT | GAT | TAT | 3514 |
| Val | Glu | Glu | Glu | Val | Tyr | Pro | Asn | Asn | Thr | Val | Thr | Cys | Asn | Asp | Tyr | |
| | | 1060 | | | | 1065 | | | | | 1070 | | | | | |

| | | | | | | | | | | | | | | | | |
|---|---|---|---|---|---|---|---|---|---|---|---|---|---|---|---|---|
| ACT | GCG | ACT | CAA | GAA | GAA | TAC | GGG | GGT | GCG | TAC | ACT | TCC | CGT | AAT | CAT | 3562 |
| Thr | Ala | Thr | Gln | Glu | Glu | Tyr | Gly | Gly | Ala | Tyr | Thr | Ser | Arg | Asn | His | |
| | 1075 | | | | 1080 | | | | | 1085 | | | | | | |
| GGA | TAT | GGC | AAA | TCT | TAT | GAA | AGT | AAT | TCT | TCC | GTA | CAA | GCT | GAT | TAT | 3610 |
| Gly | Tyr | Gly | Lys | Ser | Tyr | Glu | Ser | Asn | Ser | Ser | Val | Gln | Ala | Asp | Tyr | |
| 1090 | | | | 1095 | | | | | 1100 | | | | | | 1105 | |
| GCG | TCA | GTT | TAT | GAA | GAA | AAA | GCG | GAC | ACA | GAT | GGA | CGA | AGA | GAT | AAT | 3658 |
| Ala | Ser | Val | Tyr | Glu | Glu | Lys | Ala | Asp | Thr | Asp | Gly | Arg | Arg | Asp | Asn | |
| | | | | 1110 | | | | | 1115 | | | | | 1120 | | |
| CAT | TGC | GAA | TCT | AAC | AGA | GGG | TAT | GGG | GAT | TAC | ACG | CCA | CTA | CCA | GCT | 3706 |
| His | Cys | Glu | Ser | Asn | Arg | Gly | Tyr | Gly | Asp | Tyr | Thr | Pro | Leu | Pro | Ala | |
| | | | | 1125 | | | | 1130 | | | | | 1135 | | | |
| GGT | TAT | GTA | ACA | AAA | GAA | TTA | GAA | TAC | TTC | CCA | GAA | ACC | GAT | AAG | GTA | 3754 |
| Gly | Tyr | Val | Thr | Lys | Glu | Leu | Glu | Tyr | Phe | Pro | Glu | Thr | Asp | Lys | Val | |
| | | | 1140 | | | | 1145 | | | | | 1150 | | | | |
| TGG | GTT | GAG | ATT | GGA | GAA | ACG | GAA | GGA | ACA | TTC | ATT | GTG | GAT | AGT | GTG | 3802 |
| Trp | Val | Glu | Ile | Gly | Glu | Thr | Glu | Gly | Thr | Phe | Ile | Val | Asp | Ser | Val | |
| | 1155 | | | | | 1160 | | | | | 1165 | | | | | |
| GAA | TTA | CTC | CTT | ATG | GAG | GAA | TAAGGTATGT | TTTAAAATGT | AGCGTGTGCA | | | | | | | 3853 |
| Glu | Leu | Leu | Leu | Met | Glu | Glu | | | | | | | | | | |
| 1170 | | | | | 1175 | | | | | | | | | | | |

AATAAAGAAT GTTACTGAC CAGTATTAAC AGATAAATAA GAAACTTCTA TATAAATAAA 3913

AAACGGACAT CAATCTTAAG AGAATGATGT CCGTTTTTG TATGATTTGA TTCAACGAGT 3973

GATATGTAAA TATATTTTTT TGCGAAGTCT TTACATAACA AAAAAATTCG TATAGCAAAA 4033

TTCTAAATTT AACCTTAAAT ATAGTTAGGG TGAAAATATG CCAAACTAAT TTATTCCGAA 4093

TGTTAATTCG AAA 4106

( 2 ) INFORMATION FOR SEQ ID NO:2:

( i ) SEQUENCE CHARACTERISTICS:
        ( A ) LENGTH: 1176 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Glu | Asn | Asn | Ile | Gln | Asn | Gln | Cys | Val | Pro | Tyr | Asn | Cys | Leu | Ser |
| 1 | | | | 5 | | | | 10 | | | | | | 15 | |
| Asn | Pro | Glu | Glu | Ile | Leu | Leu | Asp | Gly | Glu | Arg | Ile | Ser | Thr | Gly | Asn |
| | | | 20 | | | | 25 | | | | | 30 | | | |
| Ser | Ser | Ile | Asp | Ile | Ser | Leu | Ser | Leu | Val | Gln | Leu | Leu | Val | Ser | Asn |
| | | 35 | | | | 40 | | | | | 45 | | | | |
| Phe | Val | Pro | Gly | Gly | Gly | Phe | Leu | Val | Gly | Leu | Leu | Asp | Phe | Val | Trp |
| | 50 | | | | 55 | | | | | 60 | | | | | |
| Gly | Ile | Val | Gly | Pro | Ser | Pro | Trp | Asp | Ala | Phe | Leu | Val | Gln | Ile | Glu |
| 65 | | | | 70 | | | | 75 | | | | | | 80 | |
| Gln | Leu | Ile | Asn | Glu | Arg | Ile | Ala | Ala | Tyr | Ala | Arg | Ser | Ala | Ala | Ile |
| | | | 85 | | | | | 90 | | | | | 95 | | |
| Ser | Asn | Leu | Glu | Gly | Leu | Gly | Asn | Asn | Phe | Asn | Ile | Tyr | Val | Glu | Ala |
| | | | 100 | | | | | 105 | | | | | 110 | | |
| Phe | Lys | Glu | Trp | Glu | Ala | Asp | Pro | Asp | Asn | Pro | Val | Thr | Arg | Thr | Arg |
| | | 115 | | | | | 120 | | | | | 125 | | | |
| Val | Val | Asp | Arg | Phe | Arg | Ile | Leu | Asp | Gly | Leu | Leu | Glu | Arg | Asp | Ile |
| | 130 | | | | | 135 | | | | | 140 | | | | |
| Pro | Ser | Phe | Arg | Ile | Ala | Gly | Phe | Glu | Val | Pro | Leu | Leu | Ser | Val | Tyr |
| 145 | | | | | 150 | | | | | 155 | | | | | 160 |

-continued

| | | | | | | | | | | | | | | |
|---|---|---|---|---|---|---|---|---|---|---|---|---|---|---|
|Ala|Gln|Ala|Ala|Asn<br>165|Leu|His|Leu|Ala|Ile<br>170|Leu|Arg|Asp|Ser|Ser Ile<br>175|
|Phe|Gly|Ala|Arg<br>180|Trp|Gly|Leu|Thr|Thr<br>185|Ile|Asn|Val|Asn|Glu<br>190|Asn Tyr|
|Asn|Arg|Leu<br>195|Ile|Arg|His|Ile|Asp<br>200|Glu|Tyr|Ala|Asn|His<br>205|Cys|Ala Asp|
|Thr|Tyr|Asn|Arg|Gly|Leu|Asn<br>215|Asn|Leu|Pro|Lys|Ser<br>220|Thr|Tyr|Gln Asp|
|Thr<br>210| | | | | | | | | | | | | | |
|Trp|Ile|Thr|Tyr|Asn|Arg<br>230|Leu|Arg|Arg|Asp|Leu<br>235|Thr|Leu|Thr|Val Leu<br>240|
|225| | | | | | | | | | | | | | |
| |Asp|Ile|Ala|Ala|Phe<br>245|Phe|Pro|Ser|Tyr|Asp<br>250|Asn|Arg|Arg|Tyr Pro Ile<br>255|
|Gln|Ser|Val|Gly<br>260|Gln|Leu|Thr|Arg|Glu<br>265|Ile|Tyr|Thr|Asp|Pro<br>270|Leu Ile|
|Thr|Phe|Asn<br>275|Pro|Gln|Leu|Gln|Ser<br>280|Val|Ala|Gln|Leu|Pro<br>285|Thr|Phe Asn|
|Val|Met<br>290|Glu|Ser|Asn|Ala|Ile|Arg<br>295|Thr|Pro|His|Leu<br>300|Phe|Asp|Val Leu|
|Asn<br>305|Asn|Leu|Thr|Ile|Phe<br>310|Thr|Asp|Trp|Phe|Ser<br>315|Val|Gly|Arg|Asn Phe<br>320|
|Tyr|Trp|Gly|Gly|His<br>325|Arg|Val|Ile|Ser|Asn<br>330|Arg|Ile|Gly|Gly|Gly Asn<br>335|
|Ile|Thr|Ser|Pro<br>340|Ile|Tyr|Gly|Arg|Glu<br>345|Ala|Asn|Gln|Glu|Pro<br>350|Pro Arg|
|Ser|Phe|Thr|Phe<br>355|Asn|Gly|Pro|Val<br>360|Phe|Arg|Thr|Leu|Ser<br>365|Asn|Pro Thr|
|Phe|Arg<br>370|Pro|Leu|Gln|Gln|Pro<br>375|Trp|Pro|Ala|Pro|Pro<br>380|Phe|Asn|Leu Arg|
|Gly|Val|Glu|Gly|Val<br>390|Glu|Phe|Ser|Thr|Pro|Leu|Asn<br>395|Ser|Phe|Thr Tyr<br>400|
|385| | | | | | | | | | | | | | |
|Arg|Gly|Arg|Gly|Thr<br>405|Val|Asp|Ser|Leu|Thr<br>410|Glu|Leu|Pro|Pro|Glu Asp<br>415|
|Asn|Ser|Val|Pro<br>420|Pro|Arg|Glu|Gly|Tyr<br>425|Ser|His|Arg|Leu|Cys<br>430|His Ala|
|Thr|Phe|Val|Gln<br>435|Arg|Ser|Gly|Thr<br>440|Pro|Phe|Leu|Thr|Thr<br>445|Gly|Pro Val|
|Phe|Ser<br>450|Trp|Thr|His|Arg|Ser<br>455|Ala|Thr|Asp|Arg|Asn<br>460|Ile|Ile|Tyr Pro|
|Asp<br>465|Val|Ile|Asn|Gln|Ile<br>470|Pro|Leu|Val|Lys|Ala<br>475|Phe|Asn|Leu|Thr Ser<br>480|
|Gly|Thr|Ser|Val|Val<br>485|Arg|Gly|Pro|Gly|Phe<br>490|Thr|Gly|Gly|Asp|Ile Ile<br>495|
|Arg|Thr|Asn|Val<br>500|Asn|Gly|Ser|Val|Leu<br>505|Ser|Met|Ser|Leu|Asn<br>510|Phe Ser|
|Asn|Thr|Thr|Leu<br>515|Gln|Arg|Tyr|Arg|Val<br>520|Arg|Val|Arg|Tyr|Ala<br>525|Ala Ser|
|Gln|Thr|Met<br>530|Val|Met|Ser|Val|Thr<br>535|Val|Gly|Gly|Ser|Thr<br>540|Thr|Gly Asn|
|Gln|Gly|Phe|Pro|Ser<br>550|Thr|Met|Ser|Ala|Asn<br>555|Gly|Ala|Leu|Thr|Ser Gln<br>560|
|545| | | | | | | | | | | | | | |
|Ser|Phe|Arg|Phe|Ala<br>565|Glu|Phe|Pro|Val|Gly<br>570|Ile|Ser|Ala|Ser|Gly Ser<br>575|
| |Gln|Gly|Ala|Ser|Ile<br>580|Ser|Ile|Ser|Asn|Asn<br>585|Val|Gly|Arg|Gln Met Phe<br>590|

```
His Leu Asp Arg Ile Glu Phe Leu Pro Val Thr Ser Thr Phe Glu Glu
        595                 600                 605
Glu Tyr Asp Leu Glu Arg Ala Gln Glu Ala Val Asn Ala Leu Phe Thr
    610                 615                 620
Ser Thr Asn Gln Leu Gly Leu Lys Thr Asp Val Thr Asp Tyr His Ile
625                 630                 635                 640
Asp Gln Val Ser Asn Leu Val Glu Cys Leu Ser Asp Glu Phe Cys Leu
                645                 650                 655
Asp Glu Lys Arg Glu Leu Ser Glu Lys Val Lys His Ala Lys Arg Leu
            660                 665                 670
Ser Asp Glu Arg Asn Leu Leu Gln Asp Arg Asn Phe Arg Ser Ile Asn
        675                 680                 685
Gly Gln Leu Asp Arg Gly Trp Arg Gly Ser Thr Asp Ile Thr Ile Gln
    690                 695                 700
Gly Gly Asp Asp Val Phe Lys Glu Asn Tyr Val Thr Leu Pro Gly Thr
705                 710                 715                 720
Phe Asp Glu Cys Tyr Pro Thr Tyr Leu Tyr Gln Lys Ile Asp Glu Ser
                725                 730                 735
Lys Leu Lys Ser Tyr Thr Arg Tyr Glu Leu Arg Gly Tyr Ile Glu Asp
            740                 745                 750
Ser Gln Asp Leu Glu Ile Tyr Leu Ile Arg Tyr Asn Ala Lys His Glu
        755                 760                 765
Ile Val Asn Val Pro Gly Thr Gly Ser Leu Trp Pro Leu Ser Ile Glu
    770                 775                 780
Asn Ser Ile Gly Pro Cys Gly Glu Pro Asn Arg Cys Ala Pro His Leu
785                 790                 795                 800
Glu Trp Asn Pro Asn Leu Asp Cys Ser Cys Arg Asp Gly Glu Lys Cys
                805                 810                 815
Ala His His Ser His His Phe Ser Leu Asp Ile Asp Val Gly Cys Thr
            820                 825                 830
Asp Leu Asn Glu Asp Leu Gly Val Trp Val Ile Phe Lys Ile Lys Thr
        835                 840                 845
Gln Asp Gly His Ala Arg Leu Gly Asn Leu Glu Phe Leu Glu Glu Lys
    850                 855                 860
Pro Leu Leu Gly Glu Ala Leu Ala Arg Val Lys Arg Ala Glu Lys Lys
865                 870                 875                 880
Trp Arg Asp Lys Arg Glu Lys Leu Glu Trp Glu Thr Asn Ile Val Tyr
                885                 890                 895
Lys Glu Ala Lys Glu Ser Val Asp Ala Leu Phe Val Asn Ser Gln Tyr
            900                 905                 910
 Asp Arg Leu Gln Ala Asp Thr Asn Ile Ala Met Ile His Ala Ala Asp
            915                 920                 925
Lys Arg Val His Arg Ile Arg Glu Ala Tyr Leu Pro Glu Leu Ser Val
    930                 935                 940
Ile Pro Gly Val Asn Ala Gly Ile Phe Glu Glu Leu Glu Gly Arg Ile
945                 950                 955                 960
Phe Thr Ala Tyr Ser Leu Tyr Asp Ala Arg Asn Val Ile Lys Asn Gly
                965                 970                 975
Asp Phe Asn Asn Gly Leu Leu Cys Trp Asn Leu Lys Gly His Val Asp
            980                 985                 990
Val Glu Glu Gln Asn Asn His Arg Ser Val Leu Val Val Pro Glu Trp
        995                 1000                1005
Glu Ala Glu Val Ser Gln Glu Val Arg Val Cys Pro Gly Arg Gly Tyr
```

|       | 1010 |     |     |     | 1015 |     |     |     |     | 1020 |     |     |     |
|-------|------|-----|-----|-----|------|-----|-----|-----|-----|------|-----|-----|-----|

Ile Leu Arg Val Thr Ala Tyr Lys Glu Gly Tyr Gly Glu Gly Cys Val
1025                     1030                1035                1040

Thr Ile His Glu Ile Glu Asp Asn Thr Asp Glu Leu Lys Phe Ser Asn
                    1045                1050                1055

Cys Val Glu Glu Glu Val Tyr Pro Asn Asn Thr Val Thr Cys Asn Asp
                1060                1065            1070

Tyr Thr Ala Thr Gln Glu Glu Tyr Gly Gly Ala Tyr Thr Ser Arg Asn
            1075                1080                1085

His Gly Tyr Gly Lys Ser Tyr Glu Ser Asn Ser Ser Val Gln Ala Asp
            1090                1095                1100

Tyr Ala Ser Val Tyr Glu Glu Lys Ala Asp Thr Asp Gly Arg Arg Asp
1105                     1110                1115                1120

Asn His Cys Glu Ser Asn Arg Gly Tyr Gly Asp Tyr Thr Pro Leu Pro
                    1125                1130                1135

Ala Gly Tyr Val Thr Lys Glu Leu Glu Tyr Phe Pro Glu Thr Asp Lys
                1140                1145                1150

Val Trp Val Glu Ile Gly Glu Thr Glu Gly Thr Phe Ile Val Asp Ser
            1155                1160                1165

Val Glu Leu Leu Leu Met Glu Glu
1170                     1175

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CTATCAGAAT TCTGGTAGTT TAAT                                              24

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CGGAGGTATT CCATGGAGGA AAATAATC                                          28

( 2 ) INFORMATION FOR SEQ ID NO:5:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CCACAGTTAC AGTCTGTAGC TCAATTACC                                         29

( 2 ) INFORMATION FOR SEQ ID NO:6:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GGTAATTGAG CTACAGACTC TAACTGTGG                                                                29

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

CGCTACTAAT AGAACCTGCA CCA                                                                      23

( 2 ) INFORMATION FOR SEQ ID NO:8:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GGTCGTGGCT ATATCCTTCG TGTCACAG                                                                 28

( 2 ) INFORMATION FOR SEQ ID NO:9:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

CCACGCTATC CACGATGAAT GTTCCTTC                                                                 28

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

TTATCTGTCG ACTATAGGTC AGTAA                                                                    25

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GGAGAAAGAT GGGGATTGAC                                                                          20

( 2 ) INFORMATION FOR SEQ ID NO:12:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
GTCATAGCTG TTTCCTG                                                              17
```

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:13:

```
CAGGAAACAG CTATGAC                                                              17
```

INSECTICIDE PROTEIN AND GENE

This is a Continuation of application Ser. No. 08/197,998, filed Feb. 16, 1994 abandoned which is a Continuation of application Ser. No. 08/102,316, filed Aug. 5, 1993, now abandoned, which is a Continuation of application Ser. No. 08/004,474, filed Jan. 14, 1993, now abandoned, which is a Continuation of application Ser. No. 07/844,302, filed Feb. 27, 1992, now abandoned.

This invention relates to a novel protein with insecticidal properties, nucleic acid sequences encoding this protein, and use of this protein to control insects.

BACKGROUND OF THE INVENTION

Many bacteria belonging to the species *Bacillus thuringiensis* (B.t.) produce crystal protein toxins which have insecticidal properties. The most studied crystal protein genes to date have been those which are active against Lepidoptera. One group of toxins, designated CryIC, has also been shown to be toxic to Spodoptera as well.

Two Spodoptera-active cryIC genes from *B.t. aizawai* and *B.t. entomocidus* have been reported by Sanchis et al, 1989, *Mol. Microbiol.* 3:229–238 and Honee et al, 1988, *Nucl. Acids Res.* 16:6240, both of which are hereby incorporated by reference. These two genes were found to code for toxins that differ by a small number of amino acid substitutions. Bosse et al, 1990, *Nucl. Acids Res.* 18:7443 describe a gene from *B.t. kenyae* which they identify as a cryIC(b), whose protein is toxic to *Bombyx mori*.

It would be desirable to identify other genes which encode toxins active against Spodoptera.

DESCRIPTION OF THE INVENTION

This invention relates to novel proteins which exhibit insecticidal activity against Lepidoptera, including Spodoptera, their nucleic acid sequences, and use of these proteins to control various insects.

In accordance with this invention, it has been found that *B.t. galleriae* strain HD29 contains DNA sequences which hybridize to the cryIC gene from *B.t. aizawai* strain HD229, yet are not significantly homologous. These new sequences have been isolated and characterized and are designated cryIC(b).

As used throughout the specification and claims, the following definitions apply:

Isolated polypeptide—a polypeptide which is no longer associated with *B.t. galleriae*, or the cell which naturally produces Substantially homologous—an amino acid sequence is substantially homologous to the full length CryIC(b) sequence if it is at least 90% homologous to CryIC(b) in the so-called "heterologous region" which occurs between amino acid 451–650, inclusive, and shows substantially the same bioactivity as CryIC(b).

Stringent hybridization conditions—those in which hybridization is effected in a standard manner at 65° C. in 4×buffered saline (a.k.a. SSPE buffer) followed by washing at 52° C. in 0.2×SSPE, which will not affect true hybrids which have formed.

Substantial bioactivity—a truncated toxin or full length polypeptide possesses substantially the same bioactivity as CryIC(b) if, in assays against Lepidopteran insects, including Spodoptera, activity is not statistically significantly different.

Truncated toxin—the portion of a protein which, after ingestion and cleavage by an insect, exhibits insecticidal activity.

Figure 1:
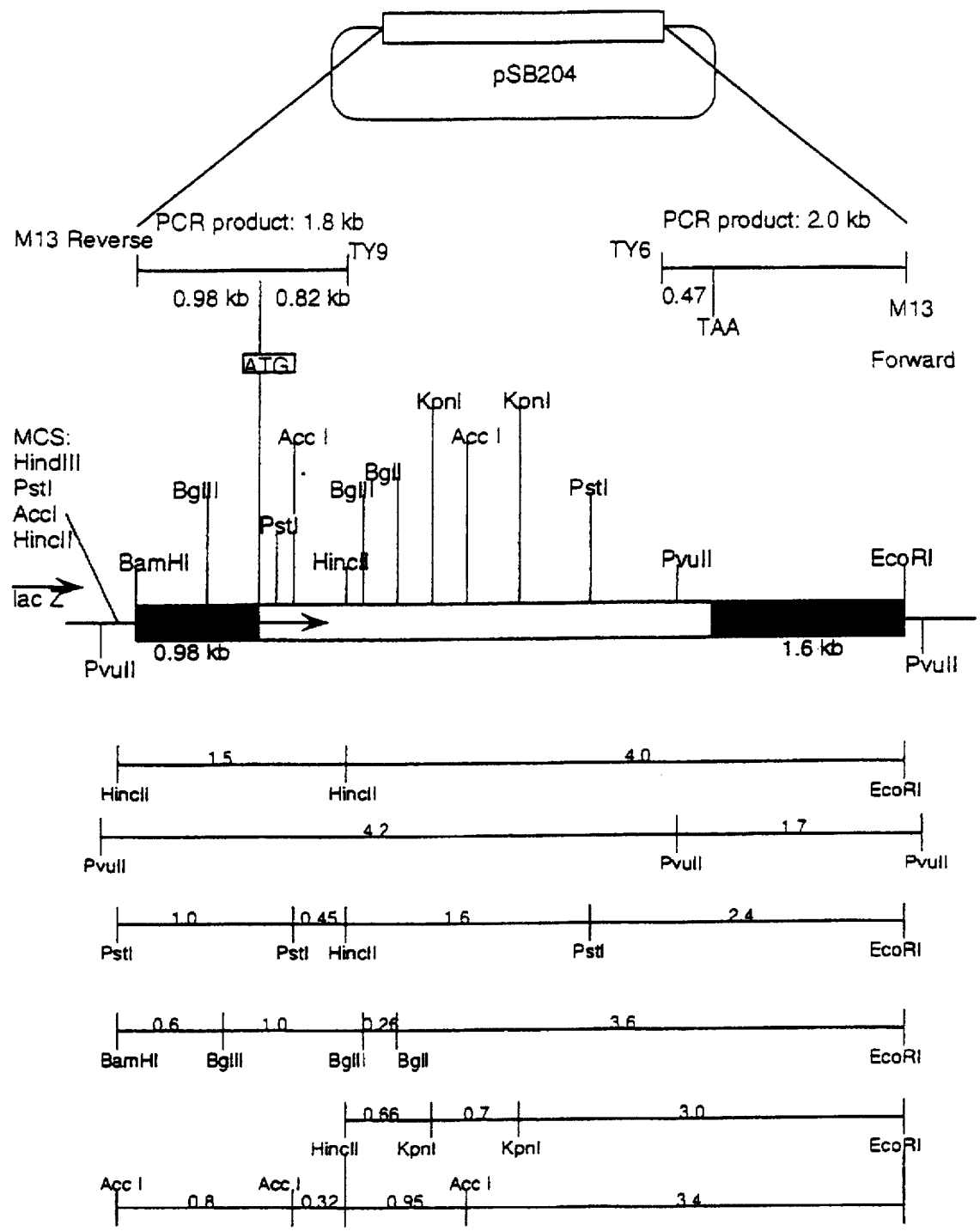
FIG. 1 is a diagram of pSB204 and the restriction sites found. Section A illustrates the result of PCR analysis which orients the cryIC(b) gene within the plasmid pSB204. The combination of M13 Reverse and TY9 primers gave a 1.8 kb product, indicating the first amino acid residue of the protein is −0.98 kb from the BamHI site in the polylinker. The combination of M13 Universal and TY6 primers gave a 2 kb product, indicating the stop codon is −1.6 kb from the EcoRI site in the polylinker. Section B is a summary of the restriction digests performed.
Figure 2:
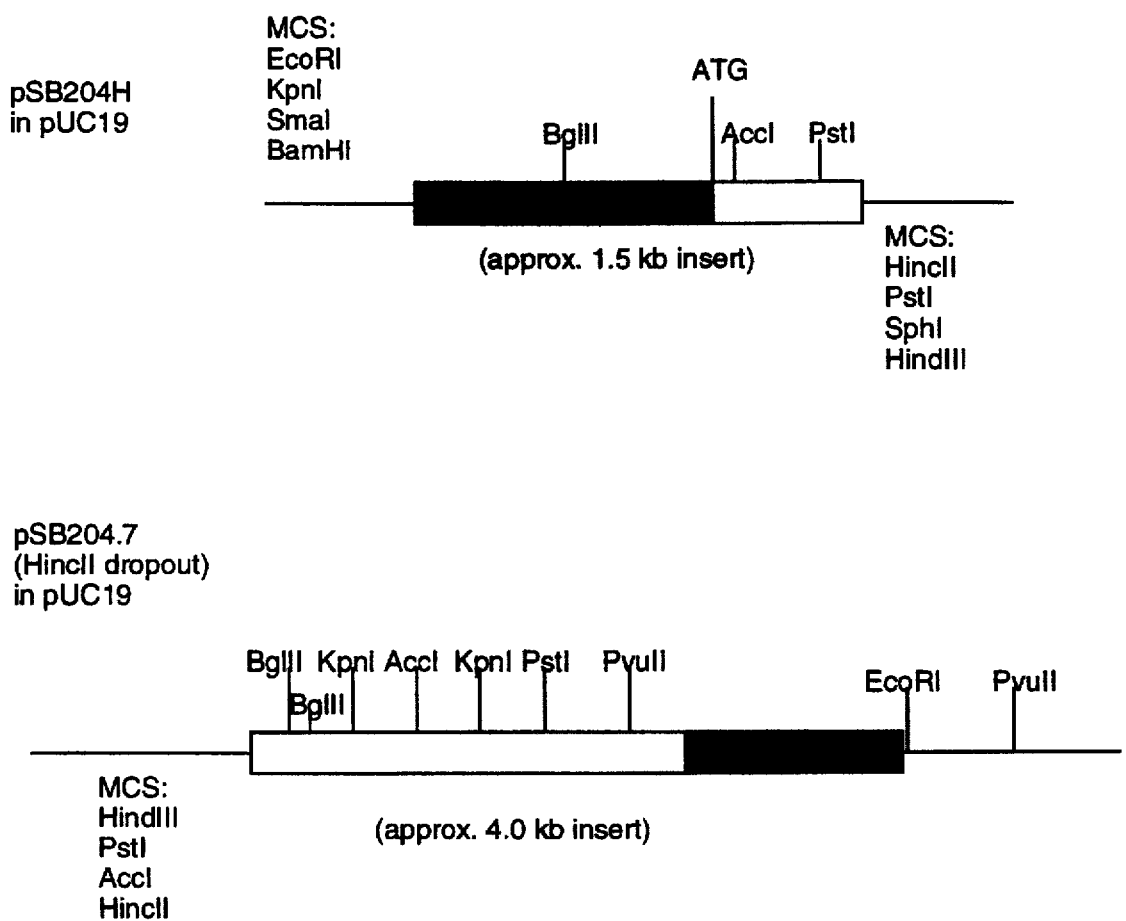
FIG. 2 illustrates two subclones used for DNA sequencing. pSB204H has a 1.5 kb HincII-BamHI fragment ligated into pUC19. pSB204.7 has the 1.5 kb HincII-BamHI piece removed, made by religating pSB204 to itself at the HincII site.
Figure 3:
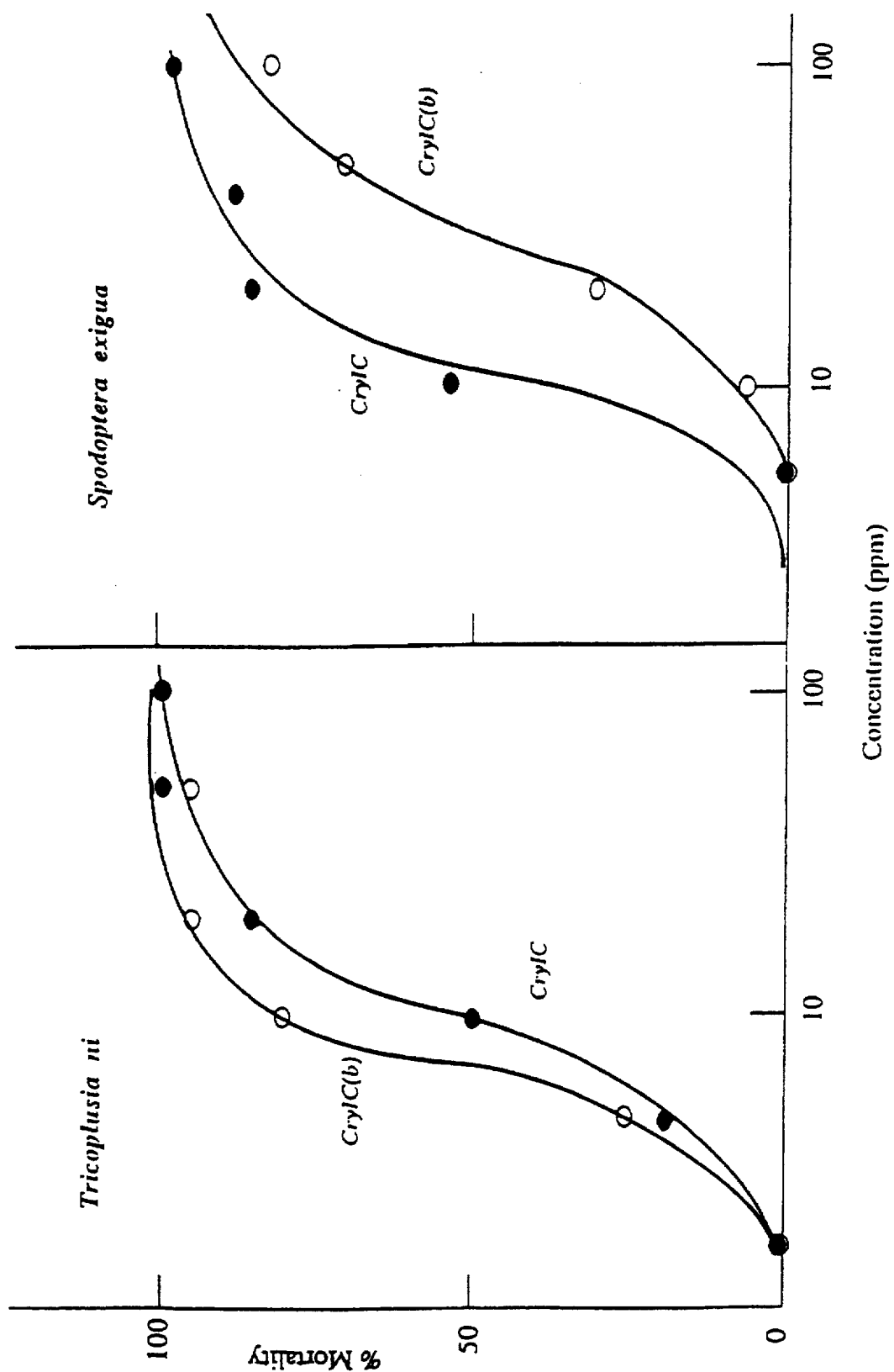
FIG. 3 shows the results of a bioassay of the CryIC(b) protein compared to CryIC in two species, *T. ni* and *S. exigua*.

The complete sequence of the novel protein is given in TABLE 1, below (SEQ. ID. NO.: 1 and SEQ. ID. NO.: 2). The CryIC(b) protein is 1176 amino acids long with a predicted molecular weight of 133 kDal. Thus one aspect of this invention comprises an isolated polypeptide having insecticidal activity characterized by having the amino acid sequence given in TABLE 1, or a polypeptide with substantial homology thereto.

It is known in the art that proteins produced by *Bacillus thuringiensis* varieties occur as a protoxin. As the insect ingests this toxin, it is cleaved, and the activated or truncated toxin then exhibits Insecticidal activity. The full length sequence discussed above is thus the protoxin form of the polypeptide. This invention also includes the truncated toxin form of the polypeptide as well.

The naturally occurring DNA sequence of the full length polypeptide has also been determined, as is given in TABLE 1 (SEQ ID NO.: 1). As is known in the art the degeneracy of the genetic code allows for various nucleic acid sequences (DNAs and RNAs) to encode the same protein. When cloning this gene in another host organism, it may prove desirable to alter the DNA codons such that those preferred by the host organism are employed, although changes are made in the translation product. Thus, all these DNAs comprise another aspect of this invention. Further, it may be desirable to clone only the truncated toxin. Thus this invention also includes nucleic acid sequences (DNAs and RNAs) which encode the truncated toxin, using either the naturally occurring codons, or other codons expressing the same amino acids. Additionally, it is recognized that minor changes in the nucleic acid sequences may result in minor changes which result in the production of a "substantially homologous" polypeptide. Thus this invention also is directed to nucleic acids which will hybridize under stringent conditions to the naturally occurring sequence.

Vectors comprising the cryIC(b) gene are yet another part of this invention. The vectors are generally a known vector, and are chosen for their suitability for use with the desired host cell. Those of ordinary skill in the art will be able to determine appropriate vectors. A gene construct is made, comprising a promoter which is expressed in the host cell, operably linked to the cryIC(b) gene of this invention; optionally ocher 3' or 5' elements which enhance expression, and known to those of ordinary skill in the art, may also be included in the construct.

A further aspect of this invention is a cell which is transformed with a vector comprising a gene encoding a polypeptide of this invention. The cell may be another prokaryotic cell, such as E. coli or other Bacillus species. Alternatively, a B.t. galleriae may be transformed with additional copies of the cryIC(b) gene to boost production of the CryIC(b) protein. Also considered as part of this invention are eukaryotic cells, especially plant cells, so that the transformed plants have insecticidal properties. Also included is a virus, such as a baculovirus which has been transformed with the cryIC(b) gene so that its native insecticidal activity is enhanced.

CryIC(b) was compared at the DNA and amino acid levels to the following published sequences of other cryI-type genes and proteins:

cryIa(a) Schnepf, et al 1985. J. Biol. Chem. 260:6264.
cryIA(b) Hofte et al. 1986. Eur.J. Biochem. 161:273.
cryIA(c) Adang et al. 1985 Gene 36:289.
cryIC Honee, et al. 1988. Nucl. Acids Res, 16:6240.
cryIC(b) Bosse et al. 1990. Nucl. Acids Res. 18:7443.
cryIE Visser et al. 1990 J. Bact., 172:6783-88.

When compared to the DNA sequence of cryIC from B.t. entomocidus, it was found that the differences between the two are limited primarily to a heterologous region between nucleotides 1646 and 2190. The overall identity between the two sequences is 87%. Comparisons were made at the amino acid level with other cryI-type protein translations in two ways: by looking at entire amino acid translations, or by dividing the translations into three regions: 1) the first 450 amino acids: 2) amino acids 451-650, which corresponds to the heterologous region and 3) amino acids 651 to the end of the translation. These results are given in TABLE 2, below. In this table, the numbers given are the % similarity/% identity.

TABLE 2

| CryIC(b) vs: | Translation Comparisons | | | |
|---|---|---|---|---|
| | 1-450* | 451-650* | 651-end* | Overall** |
| CryIC | 95/92 | 68/53 | 96/93 | 90/86 |
| CryIC(b) | 63/46 | 68/52 | 96/93 | 78/69 |
| CryIA(a) | 69/51 | 64/53 | 95/92 | 80/70 |
| CryIA(b) | 68/50 | 64/52 | 96/93 | 63/45 |
| CryIA(c) | 68/50 | 65/50 | 94/91 | 79/68 |
| CryIE | 65/49 | 68/53 | 95/93 | 79/70 |

*Bestfit (GCG, Univ. Wisconsin) computer program comparison
**Gap/Limit (GCG, Univ. Wisconsin) computer program comparison As can be seen, there is a great similarity to the CryIC protein in the first and third segments (95% and 96%), but the region between amino acids 450 and 650 only had 68% homology. When the intact translations are compared, the two showed 90% similarity at the amino acid level. When compared to the other CryI-type protein translations, there is a consistently high degree of homology with the third segment which contains the carboxy-terminal portion of the crystal protein, but none of the other comparisons, either between segments or between intact translations showed the same degree of similarity as seen with the CryIC comparisons.

The CryIC(b) protein of this invention shows toxicity towards various insects, including those of the order Lepidoptera, including Spodoptera. Thus one aspect of this invention comprises an insecticidal composition comprising as its active ingredient an insecticidal amount of a CryIC(b) protein. The CryIC(b) protein producing organism or the CryIC(b) protein may be formulated in a number of ways. For example, they may in the form of wettable powder, granules, or dusts. They may be mixed with various known theft materials including inorganic minerals or organic matter (such as hulls, corncobs, and the like). Additionally included in the formulations may be spreader-sticker adjuvants, stabilizing agents, other pesticidal additives, or equivalents. Liquid formulations may be either aqueous-based or non-aqueous based and may be foams, gels, suspensions, emulsifiable concentrates, or the like. Other ingredients including surfactants or dispersants may also be included.

The amount of active ingredient will vary depending on many factors, including the nature of the particular formulation. For dry formulations the inactive ingredient will be present in at least 1% to 95% by weight, while in liquid formulation, this amount may be somewhat reduced. The application rate will vary depending on a number of factors, including the pest to be controlled and the climatic conditions, but will generally be in the range of 0.5 to 100 kg/hectare, preferably 10-50 kg/hectare.

The following non-limiting Examples are presented to better illustrate this invention.

EXAMPLE 1

Library Construction Approximately 2 µg of B.t. galleriae genomic DNA is restricted with EcoRI and separated by electrophoresis on a 0.6% agarose gel. A slice containing fragments of approximately 9-11 kb is cut from the gel and electroeluted into 0.75 inch dialysis tubing in 0.5× TBE (Maniatis et al. 1982, Molecular Cloning: A Laboratory Manual Cold Spring Harbor Press). The eluate is purified using an Elutip-d column followed by ethanol precipitation and the resulting dried pellet is resuspended in 15 µl water to a concentration of 0.12 µg/µl.

0.2 µg of the purified 9-11 kb sized fraction is ligated to 1.0 µg of λDashII EcoRI arms (Stratagene) in a 5 µl volume under conditions recommended by the manufacturer. 1.5 µl of the ligation mixture is packaged into phage particles using the high efficiency GigaPack Gold packaging extract (Stratagene). The titre of the resulting subgenomic library is $3.1 \times 10^6$ plaque forming units per µg DNA.

Polymerase chain reaction (PCR) The oligonucleotide primers used in this study are listed in TABLE 3, below. (SEQ. ID. NOS. 3 to 10). For PCR analysis of the λ phages, 4 µl of a 100 µl phage stock is used for template DNA. Concentration of the genomic DNA in the PCR reactions is between 0.1 and 0.5 µg and the concentrations of other components are as recommended in the Perkin Elmer Cetus GeneAmp Kit. The PCR conditions used for probe generation are 25 cycles of 94° C. for 1 min, 52° C. for 2 min, and 72° C. for 3 min followed by a 7 min incubation at 72° C.

TABLE 3

OLIGONUCLEOTIDE PRIMERS

| Name | Sequence | Nt[1] | Strand[2] | Site[3] | SEQ. ID. NO. |
|---|---|---|---|---|---|
| PCR1 | CTATCAGAATTCTGGTAGTTTAAT | 3–26 | c | EcoRI | SEQ. ID. NO.: 3 |
| TY8 | CGGAGGTATTCCATGGAGGAAAATAATC | 34–61 | c | NcoI | SEQ. ID. NO.: 4 |
| galP1 | CCACAGTTACAGTCTGTAGCTCAATTACC | 871–899 | c | | SEQ. ID. NO.: 5 |
| TY9 | GGTAATTGAGCTACAGACTCTAACTGTGG | 871–899 | nc | | SEQ. ID. NO.: 6 |
| galP2 | CCGCTACTAATAGAACCTGCACCA | 1831–1854 | nc | | SEQ. ID. NO.: 7 |
| TY6 | GGTCGTGGCTATATCCTTCGTGTCACAG | 3146–3173 | c | | SEQ. ID. NO.: 8 |
| TY7 | CCACGCTATCCACGATGAATGTTCCTTC | 3566–3592 | nc | | SEQ. ID. NO.: 9 |
| PCR4 | TTATCTGTCGACTATAGGTCAGTAA | 3656–3179 | nc | SalI | SEQ. ID. NO.: 10 |

[1]The nucleotide (nt.) numbers are based on the sequence of the *B. t. entomocidus* cryIC gene in Hones et al, 1988, supra.
[2]"c" indicates that the primer matches the sequence of the coding strand and hybridizes to the noncoding strand. "nc" means that the primer sequence matches the noncoding strand.
[3]The sites listed are designed into the oligonucleotide primers to facilitate cloning by introducing nucleotide mismatches.

To generate a hybridization probe, PGR is performed using *B.t. aizawai* HD229 DNA as a template and primers galP1 and galP2 (SEQ. ID. NO.: 5 and SEQ. ID. NO.: 7). These two primers are designed to hybridize to regions of the *B.t. entomocidus* cryIC gene that are not present in the HD1 cryIA(a) gene, and the primers spanned the region which shared the least homology with the cryIA(a) gene. The resulting PCR-generated probe is a 984 bp fragment from the variable region of the *B.t. aizawai* cryIC gene.

Hybridization Screening Plaque lifts are done on the Bio-Rad Plaque Lift Membranes according to the manufacturer's instructions. Plaque lift hybridizations are performed using the same conditions as described below for Southern Blotting.

Southern Blotting Total DNA from *B.t. aizawai* strain HD229 and *B.t. galleriae* strain HD29 are restricted with EcoRI. A HindIII and an EcoRI digest are also performed on *B.t. galleriae* TY10 (which is isogeneic to strain HD29) to confirm the results. These four digests are then subjected to electrophoresis on a 0.6% agarose gel and the DNA is transferred for the gel to Zeta Probe nylon membrane using a vacuum blot apparatus. Under low stringency conditions (45° C.), the probe hybridized strongly to an 8 kb EcoRI fragment from *B.t. aizawai* HD229 and more weakly to an approximately 10 kb EcoRI fragment from *B.t. galleriae* strains PID29 and TY10. The probe also hybridizes to an approximately 14 kb HindIII fragment from strain TY10.

Phage Isolation and Characterization A subgenomic library is constructed in the λDashII vector (described supra) to isolate the *B.t. galleriae* 10 kb EcoRI fragment containing sequences which hybridize to the *B.t. aizawai* cryIC gene. Of 7800 phages that are screened, 45 are positive. Twelve of these positives are plaque purified, and the are found to fall into two classes, based on the strength of the hybridization signals. Three phages, (#7, #9, and #34) hybridize weakly and nine hybridize strongly. One of the strongly-hybridizing phages, #42, is chosen for further study.

A Southern blot is performed to identify the fragments which contain coding sequences and/or the intact gene. A 5.5 kb BamHI-EcoRI fragment is identified and subcloned in the *E. coli* vector pUC19, and this construct is referred to as pSB204.

EXAMPLE 2

Phage DNA isolation Phage DNA is isolated using Qiagen Lambda DNA columns, according to manufacturer's instructions. The phage are PEG-precipitated from a 100 ml overnight culture, treated with the buffers provided in the Qiagen Lambda kit, and purified using the Qiagen pack-500 column.

Southern transfer

Probe preparation Products form PCR are gel-purified and then radiolabelled using the Random Primers Kit from BRL under the recommended conditions. The labelled probe is separated from unincorporated label using a BioSpin columns from BioRad.

Blotting Approximately 1 µg of phage DNA is restricted with BamHI and EcoRI enzymes under high salt conditions and is electrophoresed on an 0.8% agarose/1×TBE gel. After depurinating the DNA by soaking the gel in 0.25M HCl for 10 minutes, the gel is transferred to a solution of 0.4M NaOH and vacuum blotted onto a ZetaProbe membrane (BioRad) for 30 minutes. The membrane is dried under a vacuum for 30 minutes at 80° C.

Hybridization Conditions The dried ZetaProbe membrane is prehybridized in 15 ml of 1 mM EDTA, 0.5M $NaH_2PO_4$ (pH 7.2), and 7% SDS for five minutes at 65° C. The prehybridization solution is replaced with the same solution, to which is added the denatured, labelled probe. The blot with the N-terminal probe is incubated overnight at 45° C. and the blot with the C-terminal probe is incubated at 65° C. overnight. The next day both blots are washed using the recommended conditions for ZetaProbe, except that the N-terminal blot is washed at 45° C. After air-drying, both blots are used to expose XAR film.

Polymerase Chain Reaction In addition to primers TY6, TY7,TY8, TY9, galP1 and galP2, given in Table 3, supra, three other PCR primers are made:

229C GGAGAAAGATGGGGATTGAC (SEQ. ID. NO.: 11)

M13 Forward GTCATAGCTGTTTCCTG (SEQ. ID. NO.: 12)

M13 Reverse CAGGAAACAGCTATGAC (SEQ. ID. NO.: 13)

Samples of DNA are amplified by 25 cycles of denaturing at 94° C. for one minute, annealing at 52° C. for two minutes and extending at 72° C. for three minutes.

PCR is used to demonstrate that the construct with the 5.5 kb insert carries an intact gene. The primers used were 229C, a primer based on the *B.t. entomocidus* cryIC sequence which hybridizes to the non-coding strand at 531 bp downstream of the start codon of cryIC, and TY7, which hybridizes to the coding strand at 23 bases upstream from the stop codon of the *B.t. entomocidus* sequence. The subclone of the 5.5 kb fragment is positive and generates a product of approximately 3 kb in length, which indicates that this subclone would carry an intact gene. A second set of PCRs is performed to orient the insert within the plasmid, now named pSB204. The combination of H13 Reverse and TY9 primers gives a 1.8 kb product, which indicates that the first amino acid residue of the protein is approximately 0.98 kb from the BamHI site in the polylinker of the vector. The combination of M13 Universal with TY6 primers gives a 2 kb product, indicating that the stop codon is approximately 1.6 kb from the EcoRI site in the polylinker.

A summary of the restriction digests performed is given in FIG. 1 and a list of fragment sizes generated by the restriction enzymes is given in TABLE 4, below.

TABLE 4

| Restriction Enzyme | Fragment sizes (kb) |
| --- | --- |
| PstI | 5.4, 2.1, 1.0 |
| KpnI | 7.6, 0.7 |
| SmaI | uncut |
| PvuII | 4.2, 2.4, 1.7 |
| BglII | 6.9, 1.1, 0.15 |
| HincII | 7.0, 1.45 |
| AccI | 6.1, 1.4, 0.8, 0.22 |
| BamHI + BglII | 6.3, 1.1, 0.6, 0.25 |
| BglII + HincII | 6.3, 0.8, 0.65 (2) |
| AccI + HincII | 6.1, 0.95, 0.85, 0.22 |
| KpnI + EcoRI | 4.7, 3.0, 0.7 |
| PstI + HincII | 5.4, 1.6, 0.95, 0.5 |
| PvuII + HincII | 2.4, 2.3, 1.7, 1.5, 0.6, 0.3 |

The restriction pattern of this new gene is compared to that of other cryIC genes, including B.t. entomocidus 60.5. Some similarities as well as some differences are noted. In both genes, there is an AccI site approximately 200 bp from the start codon. However, the B.t. galleriae gene is missing an AccI site found in the 3' regions of the other two cryIC genes. A PvuII site is found in the C-terminus of both these cryIC genes as well as in the 3' regions of cryIA(a), cryIA(b) and cryIC(c). Both the *B.t. galleriae* and *B.t. entomocidus* genes appear to contain a BglII site approximately 1 kb from the start codon. The *B.t. galleriae* gene contains an additional BglII site approximately 200 bp upstream of this site.

A unique HincII site is identified in the gene of this invention. The PCR data indicate that this site is approximately 550 bp downstream of the start codon. Based on this, two further subclones are created for DNA sequencing. The first, pSB204H contains a 1.5 kb HincII-BamHI fragment ligated into pUC19. The second, pSB204.7 eliminates the –5 kb HincII-BamHI fragment by religating the pSB204 plasmid to itself at the HincII site (See FIG. 2).

SDS-PAGE and Western Transfer Samples for each are prepared as follows. One ml of a two ml culture that is grown in LB for two days at 37° C. is pelleted and resuspended in 0.1 ml $H_2O$. Twenty-five μl of this is mixed with 25 μl of 2×Loading Buffer (4 ml 10% SDS, 1 ml Tris-HCl, 4 ml 50% glycerol, 0.4 ml methanol, 0.5 ml $H_2O$, 0.1 ml Bromophenol blue), and boiled for three minutes. 5 μl of this is loaded onto an 8% polyacrylamide gel. The gel is electrophoresed and then stained with Coomassie Blue. For a Western transfer, the gel is not stained, but is electroblotted onto nitrocellulose, using a standard protocol set forth below. It is then reacted with antisera that is raised using standard procedures against the purified crystals from strain SAII or PLD229.

A Southern blot is performed to locate the amino and carboxy terminal coding regions of the toxin gene within the phage. The amino terminal probe is made by PCR from 100 ng of HD229 DNA using the primers TY8 and galP2 and is approximately 1 kb in length. The carboxy terminal probe is made from 100 ng HD29 DNA using the primers TY6 and TY7 and is approximately 0.45 kb in length. Bands at 4.5 and 5.5 kb from a BamHI-EcoRI digest hybridize to both probes. These fragments are gel-purified and ligated into a pUC19 vector which is restricted with the same enzymes.

EXAMPLE 3

Sequencing of cryIC(b)

Subclone pSB204H is used to obtain the sequence to the 5' of the HincII site, and the sequence downstream of the HincII site is determined using pSB204.7. Plasmid pSB204 is used to determine the sequence through the HincII site.

Sanger dideoxy nucleotide sequencing: The T7 Sequencing Kit (Pharmacia LKB) is used to determine the sequence of both strands of the cryIC(b) gene. Compression areas are resolved using the Deaza T7 Sequencing Kit (Pharmacia). Both kits are used according to the manufacturer's recommendations. A BRL sequencing apparatus is used with BRL's Bisacrylamide:acrylamide 6% gel mix to make 49 cm×35 cm×0.4 mm sequencing gels. The gels are run using a constant power output of 55 watts and 1×TBE, diluted from a 10× stock containing 121.1 g Tris base, 55 g boric acid, and 7.4 g $Na_2EDTA$, dissolved in $H_2O$ and adjusted to a final volume of 1 liter. Running times for gels are approximately 1.5 hours for short gels and 3.5 hours for longer gels.

EXAMPLE 5

Bioassay

The CryIC(b) protein is isolated from *E. coli* cells transformed with pSB204 using the following protocol. Cells are centrifuged at 10,000 rpm for 15 min, resuspended in 10 mM Tris-HCl, pH 8 and 0.25% Tween 20/Triton X-100. Cells are centrifuged as before, then resuspended (20 ml/l broth) in 10 mM Tris-HCl, pH 8, containing 10 mM EDTA. Cells are disrupted by a French press (>20,000 lb) and centrifuged as before to collect inclusion bodies. After a saline wash, the precipitate is resuspended in water and the same volume of 1M NaCl containing 20 mM CAPS-NaOH, pH 10.5 and 2 mM EDTA. This is centrifuged as before, and the washing step is repeated twice to remove soluble proteins, then a water wash is performed. The precipitate is resuspended in 10 mM Tris-HCl, pH 8, containing 10 mM EDTA, and aliquots are frozen.

The solubilization steps are all performed over ice. 6 ml of suspension is added to 120 μl mercaptoethanol and 500 mM PMSF. 2N NaOH is added until the pH is 10.5. This is centrifuged at 15,000 rpm for 10 minutes, and column chromatography is run on the supernatant. Conditions for the chromatography are: 32×1000 mm; Sephacryl S-300 HR packing; solvent is 10 mM CAPS-NaOH, pH 10.5, 50 mM NaCl and 1 mM EDTA; speed is 90 ml/hr; monitoring is at 280 nm, 1.0 OD FS; chart speed is 0.5 mm/min; and collection is 6 in (9 ml)/tube. For acid precipitation, fractions are adjusted to pH 4.4 and incubated on ice for 1 hour, then centrifuged at 15,000 rpm for 5 min. The precipitate is dissolved in 1×TE, pH 8 and amount is estimated by measuring UV absorbance at 280 nm.

10 mls of each sample is added to 90 ml of molten insect diet (52° C.) and mixed well. Insects (10 per dose per species) are infested and mortality is recorded after four days for *S. exigua* and after 3 days for *T. ni*. Results are presented in FIG. 3 which compares CryIC and CryIC(b) proteins.

TABLE 1

SEQUENCE OF CryIC(b)

| | | | | | | |
|---|---|---|---|---|---|---|
| TAGATTTTAT | ATAAG

TABLE 1-continued

SEQUENCE OF CryIC(b)

| | | | | | | | | | | | | | | | |
|---|---|---|---|---|---|---|---|---|---|---|---|---|---|---|---|
| Ser | Val | Gly | Gln | Leu | Thr | Arg | Glu | Ile | Tyr | Thr | Asp | Pro | Leu | Ile | Thr |
| | | 260 | |

TABLE 1-continued

| SEQUENCE OF CryIC(b) | | | | | | | | | | | | | | | |
|---|---|---|---|---|---|---|---|---|---|---|---|---

TABLE 1-continued

SEQUENCE OF CryIC(b)

| | | | | | | | | | | | | | | | | |
|---|---|---|---|---|---|---|---|---|---|---|---|---|---|---|---|---|
| AGA | GAC | AAA | CGT | GAA | AAA | TTG | GAA | TGG | GAA | ACA | AAT | ATT | GTT | TAT | AAA | 2986 |
| Arg | Asp | Lys | Arg | Glu | Lys | Leu | Glu | Trp | Glu | Thr | Asn | Ile | Val | Tyr | Lys | |
| | | | 885 | | | | | 890 | | | | | 895 | | | |
| GAG | GCA | AAA | GAA | TCT | GTA | GAT | GCT | TTA | TTT | GTG | AAC | TCT | CAA | TAT | GAT | 3034 |
| Glu | Ala | Lys | Glu | Ser | Val | Asp | Ala | Leu | Phe | Val | Asn | Ser | Gln | Tyr | Asp | |
| | | 900 | | | | | 905 | | | | | 910 | | | | |
| AGA | TTA | CAA | GCG | GAT | ACG | AAT | ATC | GCG | ATG | ATT | CAT | GCG | GCA | CAT | AAA | 3082 |
| Arg | Leu | Gln | Ala | Asp | Thr | Asn | Ile | Ala | Met | Ile | His | Ala | Ala | Asp | Lys | |
| | 915 | | | | | 920 | | | | | 925 | | | | | |
| CGC | GTT | CAT | AGA | ATT | AGA | GAA | GCA | TAC | CTT | CCA | GAA | TTA | TCT | GTA | ATT | 3130 |
| Arg | Val | His | Arg | Ile | Arg | Glu | Ala | Tyr | Leu | Pro | Glu | Leu | Ser | Val | Ile | |
| 930 | | | | | 935 | | | | | 940 | | | | | 945 | |
| CCG | GGT | GTA | AAT | GCG | GGC | ATT | TTC | GAA | GAA | TTA | GAG | GGA | CGC | ATT | TTC | 3178 |
| Pro | Gly | Val | Asn | Ala | Gly | Ile | Phe | Glu | Glu | Leu | Glu | Gly | Arg | Ile | Phe | |
| | | | | 950 | | | | | 955 | | | | | 960 | | |
| ACA | GCC | TAC | TCT | CTA | TAT | CAT | GCG | AGA | AAT | GTC | ATT | AAA | AAT | CGC | GAT | 3226 |
| Thr | Ala | Tyr | Ser | Leu | Tyr | Asp | Ala | Arg | Asn | Val | Ile | Lys | Asn | Gly | Asp | |
| | | | 965 | | | | | 970 | | | | | 975 | | | |
| TTC | AAT | AAT | GGT | TTA | TTA | TGC | TGG | AAC | TTG | AAA | GGG | CAT | GTA | GAT | GTA | 3274 |
| Phe | Asn | Asn | Gly | Leu | Leu | Cys | Trp | Asn | Leu | Lys | Gly | Lys | Val | Asp | Val | |
| | | 980 | | | | | 985 | | | | | 990 | | | | |
| GAA | GAA | CAA | AAC | AAC | CAT | CGT | TCA | GTC | CTT | GTT | GTC | CCG | GAA | TGG | GAA | 3322 |
| Glu | Glu | Gln | Asn | Asn | His | Arg | Ser | Val | Leu | Val | Val | Pro | Glu | Trp | Glu | |
| | 995 | | | | | 1000 | | | | | 1005 | | | | | |
| GCA | GAG | GTG | TCC | CAA | GAA | GTT | CGT | GTC | TGT | CCA | GGT | CGT | GGC | TAT | ATC | 3370 |
| Ala | Glu | Val | Ser | Gln | Glu | Val | Arg | Val | Cys | Pro | Gly | Arg | Gly | Tyr | Ile | |
| 1010 | | | | | 1015 | | | | | 1020 | | | | | 1025 | |
| CTT | CGT | GTT | ACA | GCG | TAC | AAA | GAG | GGA | TAT | GGA | GAG | GGC | TGC | GTA | ACC | 3418 |
| Leu | Arg | Val | Thr | Ala | Tyr | Lys | Glu | Gly | Tyr | Gly | Glu | Gly | Cys | Val | Thr | |
| | | | | 1030 | | | | | 1035 | | | | | 1040 | | |
| ATT | CAT | GAG | ATC | GAA | GAC | AAT | ACA | GAC | GAA | CTG | AAA | TTT | AGC | AAC | TGT | 3466 |
| Ile | His | Glu | Ile | Glu | Asp | Asn | Thr | Asp | Glu | Leu | Lys | Phe | Ser | Asn | Cys | |
| | | | 1045 | | | | | 1050 | | | | | 1055 | | | |
| CTT | GAA | GAG | GAA | GTA | TAT | CCA | AAC | AAC | ACG | GTA | ACG | TGT | AAT | GAT | TAT | 3514 |
| Val | Glu | Glu | Glu | Val | Tyr | Pro | Asn | Asn | Thr | Val | Thr | Cys | Asn | Asp | Tyr | |
| | | 1060 | | | | | 1065 | | | | | 1070 | | | | |
| ACT | GCG | ACT | CAA | GAA | GAA | TAC | GGG | GGT | GCG | TAC | ACT | TCC | CGT | AAT | CAT | 3562 |
| Thr | Ala | Thr | Gln | Glu | Glu | Tyr | Gly | Gly | Ala | Tyr | Thr | Ser | Arg | Asn | His | |
| | 1075 | | | | | 1080 | | | | | 1085 | | | | | |
| GGA | TAT | GGC | AAA | TCT | TAT | GAA | AGT | AAT | TCT | TCC | GTA | CAA | GCT | GAT | TAT | 3610 |
| Gly | Tyr | Gly | Lys | Ser | Tyr | Glu | Ser | Asn | Ser | Ser | Val | Gln | Ala | Asp | Tyr | |
| 1090 | | | | | 1095 | | | | | 1100 | | | | | 1105 | |
| GCG | TCA | GTT | TAT | GAA | GAA | AAA | GCC | GAC | ACA | GAT | GGA | CGA | AGA | GAT | AAT | 3658 |
| Ala | Ser | Val | Tyr | Glu | Glu | Lys | Ala | Asp | Thr | Asp | Gly | Arg | Arg | Asp | Asn | |
| | | | | 1110 | | | | | 1115 | | | | | 1120 | | |
| CAT | TGC | GAA | TCT | AAC | AGA | GGG | TAT | GGG | GAT | TAC | ACG | CCA | CTA | CCA | GCT | 3706 |
| His | Cys | Glu | Ser | Asn | Arg | Gly | Tyr | Gly | Asp | Tyr | Thr | Pro | Leu | Pro | Ala | |
| | | | 1125 | | | | | 1130 | | | | | 1135 | | | |
| GGT | TAT | GTA | ACA | AAA | GAA | TTA | GAA | TAC | TTC | CCA | GAA | ACC | CAT | AAG | GTA | 3754 |
| Gly | Tyr | Val | Thr | Lys | Glu | Leu | Glu | Tyr | Phe | Pro | Glu | Thr | Asp | Lys | Val | |
| | | 1140 | | | | | 1145 | | | | | 1150 | | | | |
| TGG | GTT | GAG | ATT | GGA | GAA | ACG | GAA | GGA | ACA | TTC | ATT | GTG | GAT | AGT | GTG | 3802 |
| Trp | Val | Glu | Ile | Gly | Glu | Thr | Glu | Gly | Thr | Phe | Ile | Val | Asp | Ser | Val | |
| | 1155 | | | | | 1160 | | | | | 1165 | | | | | |
| GAA | TTA | CTC | CTT | ATG | GAG | GAA | | TAAGGTATGT | | TTTAAAATGT | | | | AGCGTGTGCA | | 3853 |
| Glu | Leu | Leu | Leu | Met | Glu | Glu | | | | | | | | | | |
| 1170 | | | | | 1175 | | | | | | | | | | | |

TABLE 1-continued

SEQUENCE OF CryIC(b)

| | | | | | | |
|---|---|---|---|---|---|---|
| AATAAAGAAT | GTTTACTGAC | GAGTATTAAC | AGATAAATAA | GAAACTTCTA | TATAAATAAA | 3913 |
| AAACGGACAT | CAATCTTAAG | AGAATGATGT | CCGTTTTTTG | TATGATTTGA | TTCAACGAGT | 3973 |
| GATATGTAAA | TATATTTTTT | TGCGAAGTCT | TTACATAACA | AAAAAATTCG | TATAGCAAAA | 4033 |
| TTCTAAATTT | AACCTTAAAT | ATAGTTAGGG | TGAAAATATG | CCAAACTAAT | TTATTCCGAA | 4093 |
| TGTTAATTCG | AAA | | | | | 4106 |

What is claimed is:

1. An isolated polypeptide having insecticidal activity characterized by having the amino acid sequence of SEQ ID No.2.

2. A nucleic acid having a sequence encoding the polypeptide of claim 1.

3. A nucleic acid according to claim 2 which is DNA.

4. A cloning vector comprising the DNA according to claim 3.

5. A cloning vector comprising a promoter operationally linked to the DNA of claim 3 and optionally other regulatory elements which enhance expression.

6. A cell comprising a vector according to claim 5.

7. A cell according to claim 6 wherein the cell is a prokaryotic cell.

8. A cell according to claim 6 wherein the cell is a plant cell.

9. A baculovirus comprising a vector according to claim 4.

10. A nucleic acid having a sequence encoding a truncated Cry IC(b) toxin polypeptide which comprises an amino acid sequence which results after an insect ingests and cleaves the polypeptide of claim 1.

11. A nucleic acid according to claim 10 which is DNA.

12. A cloning vector comprising the DNA according to claim 11.

13. A cell which is transformed with the vector of claim 12.

14. A fragment of the nucleic acid of claim 2 which comprises a sequence encoding amino acids 451–650 of SEQ ID NO:2.

15. A cloning vector comprising the nucleic acid of claim 14.

16. A cell which is transformed with the vector of claim 15.

17. A cell according to claim 16 wherein said cell is a prokaryotic cell.

18. A cell according to claim 16 wherein said cell is a plant cell.

* * * * *